United States Patent [19]

Tran

[11] Patent Number: 5,460,054
[45] Date of Patent: Oct. 24, 1995

[54] APPARATUS FOR CHOKE-FREE SAMPLING OF FLUIDS AND SLURRIES

[76] Inventor: Sa C. Tran, 529 Palencia Pl., Lakeland, Fla. 33803

[21] Appl. No.: 127,614

[22] Filed: Sep. 28, 1993

[51] Int. Cl.⁶ ................................................. G01N 1/20
[52] U.S. Cl. ..................... 73/863.61; 73/863.81; 73/864.33
[58] Field of Search ............................. 73/863.81, 863.61, 73/864.33, 863.82, 863, 52, 863.53, 863.54

[56] References Cited

U.S. PATENT DOCUMENTS

| | | |
|---|---|---|
| 2,350,323 | 6/1944 | Cochran et al. . |
| 2,475,857 | 7/1949 | Reinert . |
| 2,608,866 | 9/1952 | Breedlove et al. . |
| 2,955,469 | 10/1960 | Marble . |
| 3,381,537 | 5/1968 | Goodson et al. . |
| 3,429,186 | 2/1969 | Price et al. . |
| 3,595,087 | 7/1971 | Starks ................................ 73/863.54 |
| 3,638,498 | 2/1972 | Nelms ............................ 73/863.61 X |
| 3,659,461 | 5/1972 | Thompson .......................... 73/863.54 |
| 3,681,997 | 8/1972 | Allen et al. . |
| 3,765,226 | 10/1973 | Strickland et al. ............. 73/863.61 X |
| 4,018,089 | 4/1977 | Dzula et al. .................... 73/863.61 X |
| 4,080,831 | 3/1978 | Roberts et al. .................. 73/863.61 |
| 4,167,117 | 9/1979 | Stokley et al. ................. 73/863.61 X |
| 4,307,620 | 12/1981 | Jiskout ........................... 73/863.61 X |
| 4,562,747 | 1/1986 | Jaeger ............................ 73/863.53 X |
| 4,918,999 | 4/1990 | Wenshau et al. ................... 73/863.54 |
| 5,341,690 | 8/1994 | Dawson et al. .................... 73/863.61 |

*Primary Examiner*—Thomas P. Noland
*Attorney, Agent, or Firm*—Shlesinger, Arkwright & Garvey

[57] ABSTRACT

An apparatus for choke-free sampling of fluids or slurries flowing in a main process conduit has a sampling circuit including inlet, outlet and sample collection mechanism. The inlet communicates with the process conduit at an angle to the process conduit. The outlet communicates with process conduit downstream of the inlet. An external water-kicker source is provided for accelerating sample fluid flow into the inlet.

20 Claims, 4 Drawing Sheets

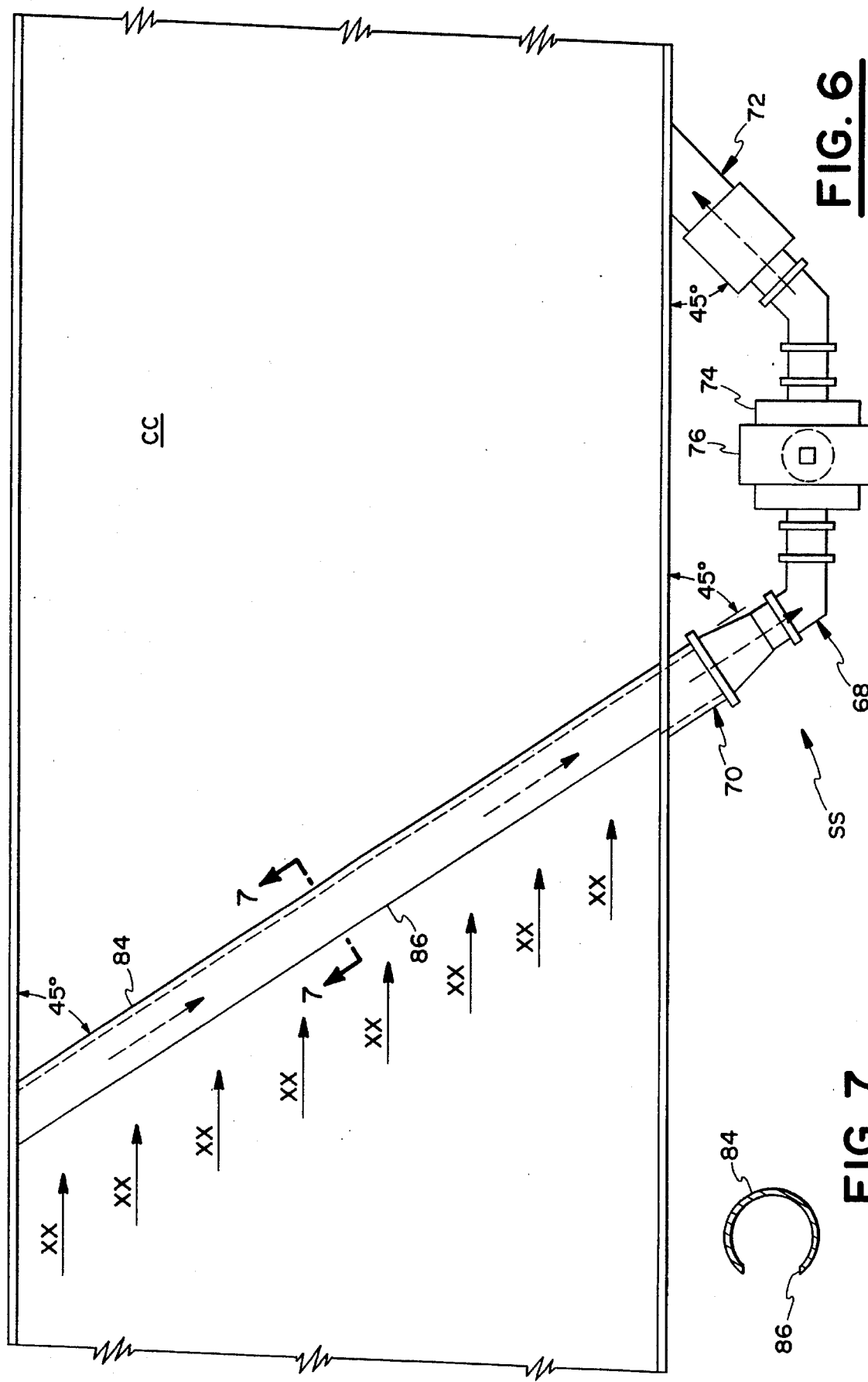

APPARATUS FOR CHOKE-FREE SAMPLING OF FLUIDS AND SLURRIES

FIELD AND HISTORICAL BACKGROUND OF THE INVENTION

The present invention is directed to obtaining samples of fluids or slurries, and more particularly to an apparatus for choke-free sampling of fluids or slurries flowing in a main process conduit.

Sampling slurries is still a big challenge in the industry, especially in the phosphate mining application. Particularly, tap and penetration type samplers have been used in the benefication (float and washer) and phosphoric acid plants. However, much difficulty has been experienced in operating and maintaining these types of samplers. The most significant of which has been excessive wear and choking. In order to keep the samplers in working order, weekly maintenance have been required at the benefication plant, and monthly maintenance have been required at the phosphoric acid plants.

Various types of sampling devices have been proposed in the art and are disclosed in U.S. Pat. Nos. 2,350,323; 2,475,857; 2,608,866; 2,955,469; 3,381,537; 3,429,186; 3,681,997; and 4,167,117.

There remains a need in the art, however, for a fluid or slurry sampling device which reduces the impact of wearing and choking.

OBJECTS AND SUMMARY OF THE INVENTION

The principal object of the present invention is to provide an improved apparatus for sampling a fluid or slurry flowing in a main process conduit, in which a portion of the fluid or slurry flows continuously, without choking through the sample circuit.

Another object of the present invention is to provide an apparatus for sampling a fluid or slurry flowing in a main process conduit, in which the impact of excessive wear and choking is significantly reduced.

Yet another object of the present invention is to provide an apparatus for sampling a fluid or slurry flowing in a main process conduit, in which any friction in the sample circuit is substantially reduced thereby assuring a smooth and uninterrupted flow of the fluid or slurry through the sample circuit.

An additional object of the present invention is to provide an apparatus for sampling a fluid or slurry flowing in a main process conduit, wherein true and accurate samples are obtained.

Yet an additional object of the present invention is to provide an apparatus for sampling a fluid or slurry flowing in a main process conduit, wherein the sample circuit is connected in parallel to the process conduit thereby assuring that the fluid or slurry is able to enter and pass through the sample circuit, and return to the main process conduit.

Still yet an additional object of the present invention is to provide an apparatus for sampling a fluid or slurry flowing in a main process conduit, which significantly reduces the extent of maintenance required to keep the apparatus in good working condition.

A further object of the present invention is to provide an apparatus for sampling a fluid or slurry flowing in a main process conduit, which is versatile and universal in application. It can be used for practically any type of flow at different pressures simply by selecting appropriate sample value and fittings.

In summary, the main object of the present invention is to provide an apparatus for sampling a fluid or slurry flowing in a main process conduit, in which the impact of wearing and choking on obtaining a true and accurate sample of the material is significantly reduced, and in which the amount of maintenance required to keep the apparatus in good working condition is minimum.

BRIEF DESCRIPTION OF THE DRAWINGS

The above and other objects and advantages and novel features of the present invention will become apparent from the following detailed description of the invention illustrated in the accompanying drawings, wherein:

FIG. 3 is an illustration of the sample circuit valve shown in the closed position;

FIG. 4 is an illustration of the sample circuit valve shown in the open position for obtaining a sample of the fluid;

FIG. 6 is a schematic illustration of the third embodiment of the invention;

FIG. 7 is a partial enlarged sectional view taken along line 7–7 of FIG. 6;

DETAILED DESCRIPTION OF THE INVENTION

Figure 1:
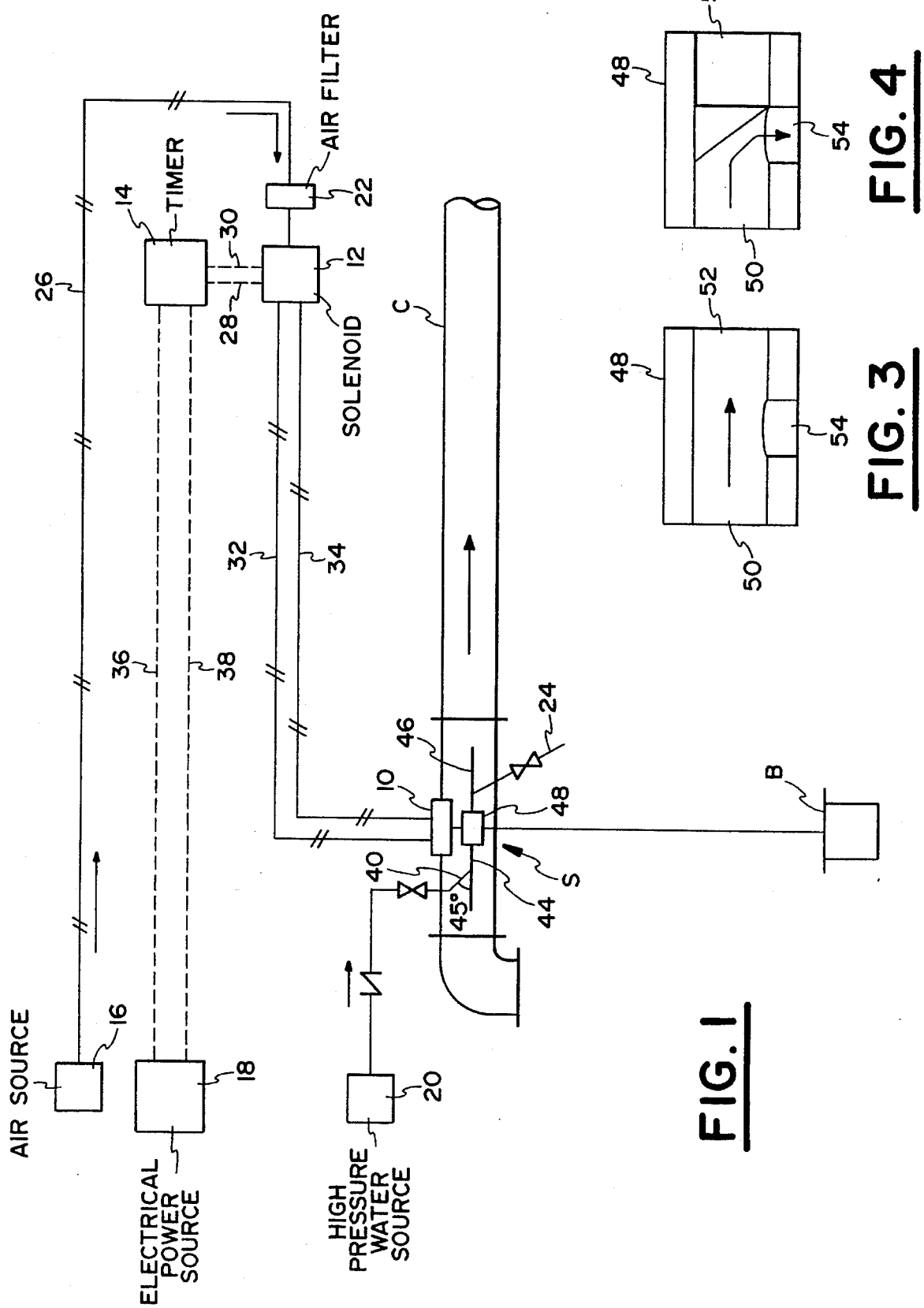
FIG. 1 is a schematic illustration of a sampling operation shown with the apparatus of the present invention.

As illustrated in FIG. 1, the sampling apparatus or sampler S of the present invention is connected in parallel to main process pipe or conduit C. The apparatus S is preferably mounted on the horizontal plane and immediately downstream from a pump discharge or pipe fittings, where the flow is turbulent. A catcher bag B is connected to sampler S for collecting and storing samples. By using a pneumatic double-acting actuator 10, in combination with four-way solenoid 12 and digital timer unit 14 including two timers, sampler S can be set to operate automatically at any preferred pre-selected time interval to obtain a representative sample in accordance with the process variability.

In FIG. 1, reference numerals 16 and 18 designate air and electrical power sources, respectively, and numeral 20 designates a source of high pressure water the function of which is described below in detail. A air filter 22 is placed in-line with air source 16. A bleeder valve mechanism 24 is connected to sampler S, which is normally closed, but can be opened for cleaning purposes. The solenoid 12 is connected to air source 16 by line 26, to timer 14 by lines 28 and 30 and to pneumatic actuator 10 by lines 32 and 34. The timer 14 is connected to electrical source 18 by lines 36 and 38. Likewise, water source 20 is connected to sampler S by line 40.

Figure 2:
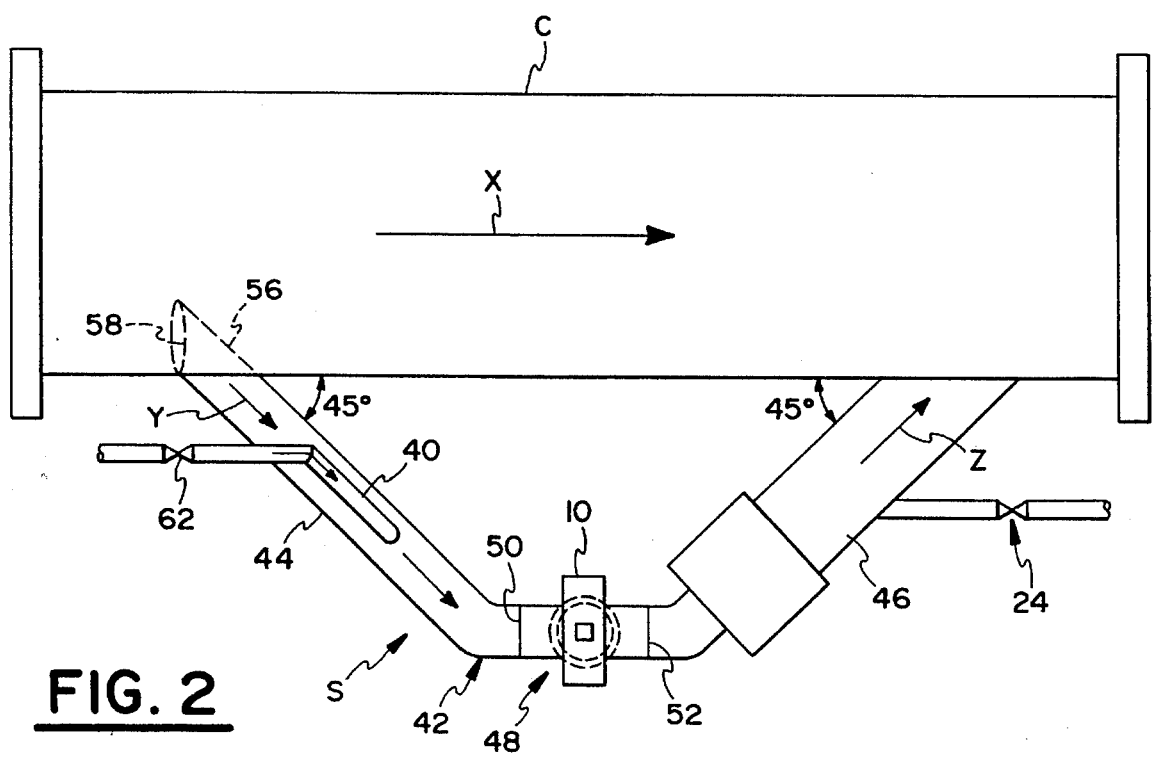
FIG. 2 is a schematic illustration of the apparatus of the present invention shown, in top plan view, connected to a main process conduit.

As shown in detail in FIG. 2, sampler S includes sample collecting device or circuit 42 which includes sampler intake and return lines 44 and 46, respectively. The inside diameter of return line 46 is significantly larger, preferably twice, than the inside diameter of intake line 44 to help create a "vacuum" or "pull" effect in circuit 42. This "vacuum" or "pull" effect is described below in detail.

A conventional three-way sampling valve 48 is positioned between lines 44 and 46. Normally, intake and return ports 50 and 52 are kept open such that the fluid or slurry flowing in conduit C (shown by arrow X) also flows through sample collection circuit 42, shown by arrows Y and Z. Port 54, which is normally kept in the closed position (FIG. 3), can be opened (FIG. 4) by activating pneumatic actuator 10 to direct the flow of the fluid or slurry toward sample collection bag B. Both the sample intake and return lines 44 and 46, communicate with conduit C at an angle of about 45° or less. A sample probe or bumper 56 extends into conduit C and is in fluid communication with sample intake line 44. Typically, it is the end section of sample intake line 44 that extends into the process fluid flow to function as the sample probe. Probe opening 58 faces upstream to collect, push and guide a portion of the process fluid flow toward sampler S. This is the "push" effect of the bumper 56. Preferably, probe 56 has a minimum length corresponding to about twice the inside diameter of intake line 44, and a maximum length corresponding to about 1.414 times the inside diameter of process conduit C. As one of ordinary skill in the art would appreciate, the probe opening 58 is generally oblong or elliptical in shape. Preferably, opening 58 has a length of about 1.414 times the inside diameter of intake line 44, with the width corresponding to the inside diameter of line 44.

As noted above, an external source of high pressure kicker water 20 is in fluid communication with sampler S. In particular, the external water source line 40 communicates with sample intake line 44 at an angle of about 50°–65°, and preferably 45° relative to the center line of the sample intake line 44 (see FIG. 1). (It should be noted that while water, for the reasons of economy and easy availability, is a preferable medium for accelerating and improving the flow of the process fluid through the sampler 8, other compatible fluids, may also be used for an effective operation.)

As noted above, water is discharged into sample intake line 44 and flows in the same direction as the sample fluid from conduit C, and creates the "pull" effect. In other words, as a result of the high pressure water flowing in the same direction as the sample fluid, the flow of the fluid or slurry from the main process conduit C is boosted, and the sample fluid flows faster and creates a vacuum behind its entrance point at opening 58, thereby creating a "pull" effect. The water also helps to decrease friction in the sample circuit 42, thereby significantly reducing the choking and wearing problems. This "pull" effect of the high pressure water, in combination with the "push" effect of the sample probe 56, defined above, is called the "push-pull" effect. Further, the main fluid or slurry stream inside conduit C continuously bombards the probe 56, thereby creating a turbulence in the vicinity. This turbulence, together with the "push-pull" effect, produces the "turbulent, push-pull" effect assisting in obtaining a true and accurate sample flow through sample collection circuit 42. In order for an effective operation of sampler S, the pressure of the external water must be kept at a level higher than the fluid pressure in conduit C. The operation of the external high pressure water source 20 is controlled by gate valve 62. It should be noted that in addition to improving the flow of the process fluid from the main process line (conduit C) toward and through sample collection circuit 42, the external kicker water produces another advantage, in the event the process flow is stopped. In particular, the external water removes from circuit 42 any sample fluid remaining therein, thereby preventing choking of the sampler S when process flow resumes. The external kicker water source 20 further prevents the occurrence of choking and reduces resistance which is the main cause of the sample circuit wear.

Figure 5:
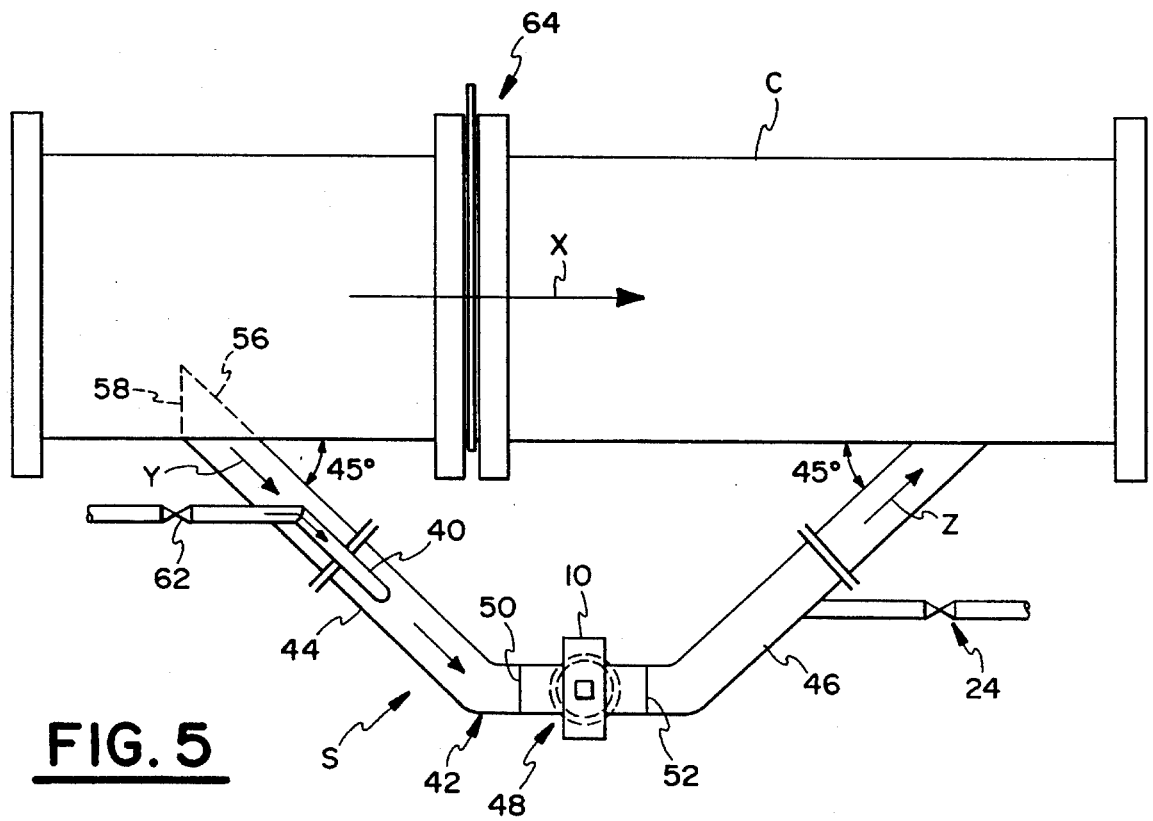
FIG. 5 is a schematic illustration of the second embodiment of the present invention.

The embodiment shown in FIG. 5 is similar to the sampler S shown in FIG. 2, with the exception that an orifice plate 64 is placed in the flow of main process fluid and the use of sample probe is optional. (In this embodiment, like parts/components are designated with the same reference numerals as in the first embodiment.)

This particular arrangement is used in the applications where external water is not available or cannot be introduced to the sample and/or process. (The external water source may, however, be used for cleaning sample collection circuit 42.) In this embodiment, in order to create a flow through sample circuit 42, a pressure differential must exist across the sampler S. To meet this criteria, an orifice plate 64 is installed in conduit C. The plate 64, as shown in FIG. 5, extends perpendicularly into the flow of the process fluid flowing in conduit C. The orifice plate 64 creates a pressure differential across sampler S, thereby producing a flow of process fluid or slurry through the sample circuit 42. In particular, the pressure of the process fluid on the upstream side of orifice plate 64 is higher than the downstream side. In this embodiment, the use of a sample probe, although not necessary, is recommended. Further, in this embodiment, the diameter of return line 46 is the same as the diameter of intake line 44.

Figure 8:
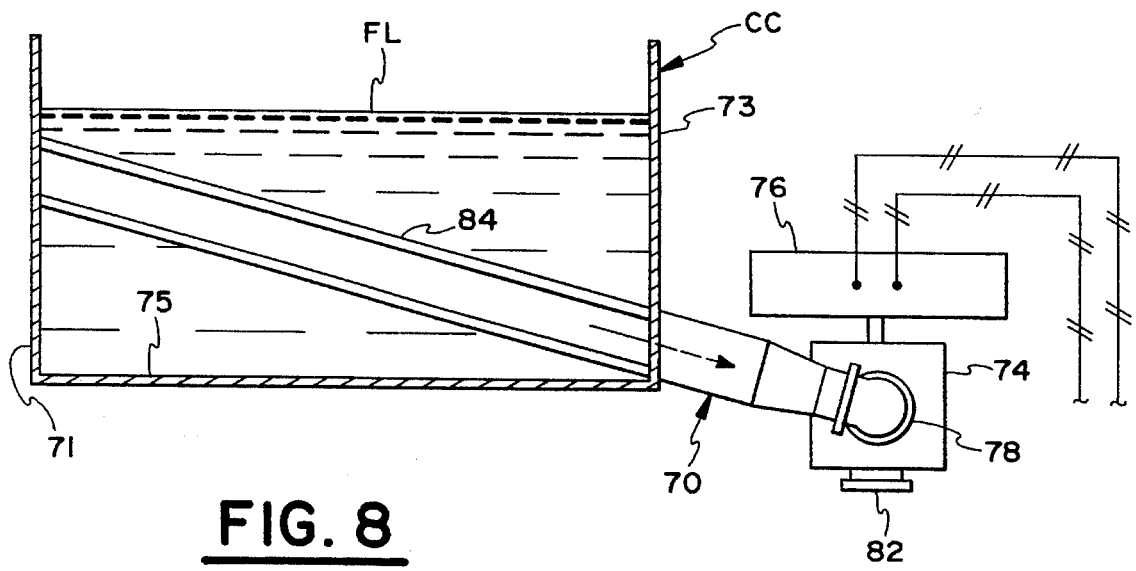
FIG. 8 is an end view of the apparatus shown in FIG. 6.
Figure 9:
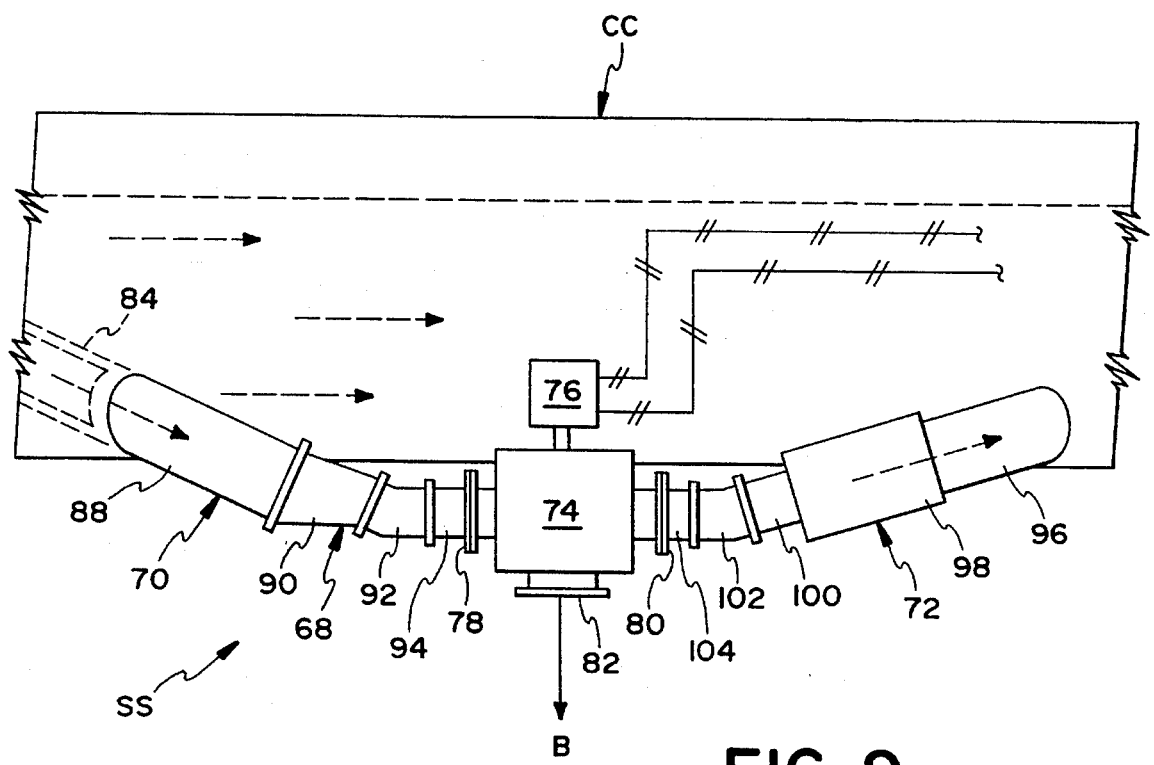
FIG. 9 is a front elevational view of the apparatus shown in FIG. 6.

FIGS. 7–9 disclose a third embodiment of the invention, which is similar to the second embodiment disclosed in FIG. 5, with the exception that external kicker water is not required, but a longer sample probe or bumper is necessary. This embodiment of the invention is ideal and suited for launder gravity flow applications and the like.

As best shown in FIGS. 6 and 9, the sampler SS includes sample collection circuit 68 connected to main process line or conduit CC by sampler intake and return lines 70 and 72. The lines 70 and 72 are each connected with the conduit CC at an angle of about 45° or less. A three-way valve 74, similar to valve 48, connects intake and return line 70 and 72. As in the previous embodiments, a pneumatic actuator 76 is provided to operate sampler SS. The mechanism for activating actuator 76 is similar to the activating mechanism disclosed above in connection with the first and second embodiments. The valve 74 has intake and return ports 78 and 80, which are in fluid communication with intake and return lines 70 and 72, respectively. Sample collection port 82 is in fluid communication with the line to a sample bag similar to the sample bag B described above.

A sample probe or bumper 84, which is generally C-shaped in cross-section, extends into the process conduit CC and is in fluid communication with sample intake line 70. The sample probe opening 86 faces upstream and, since the probe 84 is inclined downstream of the fluid flow in the conduit CC, the process fluid is directed into probe 84, collected and moved downwardly toward collection circuit 68. The process of sample collection and smooth and continuous flow toward collection circuit 68, is further facilitated by the fact that probe 84 and sample intake line 70 are downwardly inclined toward valve 74, and about 15.5° relative to the bottom 75 of launder (conduit CC). Further, probe 84 extends from one side 71 of the launder to its other side 73 to provide a maximum probe length (see FIGS. 8 and 9). The downward inclination of probe 84, and its maximum length within conduit CC from side 71 to side 73, would vary in accordance with the fluid level FL and the width of conduit CC.

The area of probe opening 86 is, preferably, about between one-half and one-third of the total area of the probe 84 (see FIG. 7). The probe length can additionally be set as described above in connection with the first and second embodiments. Further, probe 84 extends into process conduit CC at an angle of about 45° or less, corresponding to the angle of sample intake line 70, relative to the process conduit CO. In FIG. 6, arrows XX indicate the direction of fluid flow in conduit CC and illustrate collection of a true and accurate sample from different layers of fluid by the sampler SS.

As best shown in FIG. 9, sample intake line 70 is comprised of a main pipe 88, reducer 90, elbow 92 and nipple 94, all connected in succession toward valve 74. The return line 72 is likewise comprised of main pipe 96, reducer 98, nipple 100, elbow 102, and nipple 104, also connected in succession toward valve 74. It should be noted that other mechanical components can be used without departing from the spirit of the invention and for an effective operation of the sampler SS.

As best shown in FIG. 9, sample collection circuit 68 is oriented horizontally somewhat below the process conduit CC. This particular orientation of the overall sample collection circuit 68, together with downward inclination of probe 84 and sample intake line 70, causes the process fluid to flow into the sampler SS by gravity.

Although not shown, pneumatic actuator 76 is also connected to electronic and pneumatic circuitry and other related components in a similar fashion as shown and described above in connection with sampler S.

The automatic function of the sampler of the invention is obtained by coordinating the timer (14), the solenoid (12), and the pneumatic actuator (10 or 76). Depending upon the particular application, sample output, sample cycle, and sample duration can be easily selected by manipulating the electronic controls. Preferably, one timer circuit is set at 0.1 seconds to 60 seconds, and the other timer circuit is selected at 1 minute to 60 minutes. Timer cycle is set at 2 or more seconds for sample output at every 10 or more minutes depending upon the user's preference. Sample output can be adjusted to meet a specific sample requirement by varying the time sequence. One of ordinary skill in the art would appreciate that the time sequence controls the solenoid valve, which in turn activates the pneumatic actuator. The sample valve (48 or 74) is opened or closed by the pneumatic actuator (10 or 76). Therefore, the sampler can be set to operate automatically at any preferred timed interval to obtain a representative sample in accordance with the process variability.

While this invention has been described as having preferred designs, it is understood that it is capable of further modifications, uses and/or adaptations following in general the principle of the invention and including such departures from the present disclosure as come within the known or customary practice in the art to which the invention pertains, and as may be applied to the central features hereinbefore set forth, and fall within the scope of the invention and of the limits of the appended claims.

What I claim is:

1. An apparatus for choke-free sampling of a slurry fluid flowing in a main process conduit, comprising:

a) sampling means including inlet, outlet, and sample collecting means;

b) said inlet extending into the process conduit at an angle relative thereto;

c) said outlet communicating with the process conduit downstream of said inlet;

d) means in communication with said sampling means for accelerating the fluid flow into said inlet;

e) said inlet including an opening facing the fluid flow in the process conduit;

f) said sampling means including a sample collection circuit;

g) means for flowing the fluid continuously through said sample collection circuit; and h) wherein the fluid flows in a generally common direction through the process conduit and said sample collection circuit.

2. The apparatus of claim 1, wherein:

a) said inlet extends into the conduit at an angle of up to about 45° relative thereto.

3. The apparatus of claim 1, wherein:

a) said outlet communicates with the conduit at an angle of up to about 45° relative thereto.

4. The apparatus of claim 1, wherein:

a) said sampling means further includes sample intake and sample return lines connected respectively to said inlet and outlet.

5. The apparatus of claim 4, wherein:

a) said fluid flow accelerating means comprises a source for supplying a high pressure auxiliary fluid.

6. The apparatus of claim 5, wherein:

a) said auxiliary fluid supply source communicates with said sample intake line at an angle of about 50°–65°.

7. The apparatus of claim 5, wherein:

a) said auxiliary fluid supply source communicates with said sample intake line at an angle of about 45°.

8. The apparatus of claim 5, wherein:

a) said auxiliary fluid source supplies water at a pressure higher than the pressure of the sample fluid.

9. The apparatus of claim 4, wherein:

a) said sample intake line has an inside diameter; and b) said inlet has a length corresponding to twice the inside diameter of said sample intake line.

10. The apparatus of claim 4, wherein:

a) said inlet is longer in length than the diameter of the process conduit.

11. The apparatus of claim 4, wherein:

a) the diameter of said sample return line is larger than the diameter of said sample intake line.

12. An apparatus for choke-free sampling of a slurry fluid flowing in a main process conduit, comprising:

a) sampling means including sample intake and return lines;

b) said sampling means including sample collecting means connected to said sample intake and return lines;

c) said sample intake line communicating with the process conduit at an angle of up to about 45°;

d) said sample return line communicating with the process conduit at an angle of up to about 45° and downstream of said sample intake line;

e) means positioned in the process conduit downstream of said sample intake for creating differential pressure across said sampling means to thereby effect a continuous flow of the sampling fluid through said sampling means;

f) said sample intake and return lines both being positioned on the same side of the process conduit;

g) said sample intake line including an opening facing the fluid flow in the process conduit;

h) said sampling means including a sample collection circuit;

i) means for flowing the fluid continuously through said sample collection circuit; and j) wherein the fluid flows in a generally common direction though the process conduit and said sample collection circuit.

13. The apparatus of claim 12, and including:

a) a sample probe in communication with said sample intake line and extending into the process conduit.

14. The apparatus of claim 12, wherein:

a) the diameter of said sample intake line corresponds with the diameter of said sample return line.

15. The apparatus of claim 12, and including:

a) means in communication with said sampling means for discharging a high pressure fluid into said sample intake line.

16. An apparatus for choke-free sampling of a slurry fluid flowing in a main process conduit, comprising:

a) sampling means including sample intake and return lines;

b) said sampling means including sample collecting means connected to said sample intake and return lines;

c) said sample intake line communicating with the process conduit at an angle of up to about 45°;

d) said sample return line communicating with the process conduit at an angle of up to about 45° and downstream of said sample intake line;

e) a sample probe in communication with said sample intake line and extending into the process conduit;

f) said sample probe being inclined in the direction of fluid flow in the process conduit;

g) said sample intake and return lines both being positioned on the same side of the process conduit;

h) said sample probe including an opening facing the fluid flow in the process conduit;

i) said sampling means including a sample collection circuit;

j) means for flowing the fluid continuously through said sample collection circuit; and k) wherein the fluid flows in a generally common direction through the process conduit and said sample collection circuit.

17. The apparatus of claim 16, wherein:

a) said sample intake and return lines are inclined downwardly away from the process conduit.

18. The apparatus of claim 16, wherein:

a) said sample probe is generally C-shaped in cross-section.

19. The apparatus of claim 16, wherein:

a) said sample probe is inclined downwardly toward said sample intake line.

20. The apparatus of claim 16, wherein:

a) said sample probe extends from one side of the process conduit to an opposite side thereof.

* * * * *